(12) United States Patent
Shin et al.

(10) Patent No.: US 8,372,132 B2
(45) Date of Patent: Feb. 12, 2013

(54) STENT INSERTING DEVICE

(75) Inventors: Kyong-Min Shin, Seoul (KR); Sung-Min Kim, Seoul (KR)

(73) Assignees: Taewoong Medical Co. Ltd., Kyunggi-do (KR); Kyong-Min Shin, Seoul (KR)

( * ) Notice: Subject to any disclaimer, the term of this patent is extended or adjusted under 35 U.S.C. 154(b) by 549 days.

(21) Appl. No.: 12/070,095

(22) Filed: Feb. 14, 2008

(65) Prior Publication Data

US 2008/0262591 A1   Oct. 23, 2008

(30) Foreign Application Priority Data

Apr. 23, 2007   (KR) .................. 10-2007-0039377

(51) Int. Cl.
*A61F 2/06* (2006.01)
(52) U.S. Cl. ..................................................... 623/1.11
(58) Field of Classification Search .............. 623/1.11, 623/1.12, 1.13; 606/108, 191, 194, 198, 606/200
See application file for complete search history.

(56) References Cited

U.S. PATENT DOCUMENTS

2002/0055766 A1*  5/2002  Wallace et al. ............. 623/1.11
2005/0080474 A1*  4/2005  Andreas et al. ............. 623/1.11
2006/0025844 A1*  2/2006  Majercak et al. ........... 623/1.11

FOREIGN PATENT DOCUMENTS

EP           696447 A2 *  2/1996

OTHER PUBLICATIONS

Dictionary definition of the term "over." <http://www.thefreedictionary.com/over>.*

* cited by examiner

*Primary Examiner* — Tuan V Nguyen
*Assistant Examiner* — Katherine M Shi
(74) *Attorney, Agent, or Firm* — IP & T Group LLP

(57) ABSTRACT

A stent inserting device is used in inserting a self-expandable stent with leading and trailing ends into a tubular organ of a living body. The stent inserting device includes a grip body, an external tube attached to a front end of the grip body, a push member movably inserted into the external tube from a rear end of the grip body, and a tubular cap for removably receiving the stent in a compressed state. The tubular cap has a front end operatively connected to the push member and a rear end slidably fitted to a front end of the external tube. The stent inserting device is designed to hold the stent within the tubular cap in such a manner that the stent is first expanded at the trailing end and then gradually expanded toward the leading end when the tubular cap is pushed away from the external tube.

4 Claims, 4 Drawing Sheets

STENT INSERTING DEVICE

FIELD OF THE INVENTION

The present invention relates to a stent inserting device for inserting a stent into a stenosal portion of tubular organs of a living body such as an esophagus and the like to expand the stenosal portion and, more particularly, to a stent inserting device that can allow a stent to be first expanded at its trailing end and then gradually expanded toward its leading end within a stenosal portion of tubular organs and, therefore, can be effectively used in treating the stenosal portion where the position of a trailing end of the stent needs to be controlled accurately.

BACKGROUND OF THE INVENTION

There are generally known various kinds of methods for treating a stenosal portion of tubular organs of a living body such as an esophagus and the like without resort to a surgical operation. One of the known treatment methods is to use a self-expandable stent made of a super-elastic shape memory alloy. The term "stenosal portion" used herein refers to a bodily portion where stenosis is in progress or has been already completed.

In the stent-used treatment method, a cylindrical stent of specified length is formed by weaving super-elastic shape memory alloy wires. The stent is inserted into a stenosal portion of tubular organs of a living body with the volume thereof kept minimized. As the stent is set free and returned back to its original shape, the stenosal portion is expanded outwardly by the stent.

A separate stent inserting device is required in the stent-used treatment method in order to insert the stent into the stenosal portion of tubular organs. One example of conventional stent inserting devices is shown in FIG. 1. Referring to FIG. 1, the stent inserting device includes a grip body 2, an external tube 3 connected to the grip body 2 and an internal tube 5 inserted into the external tube 3 for movement in a forward or backward direction. A self-expandable stent 1 is slidably held within a tip end portion of the external tube 3 in a compressed state. The stent 1 is pushed out of the external tube 3 by means of the internal tube 5.

In the stent inserting device configured as above, the tip end portion of the external tube 3 in which the stent 1 is fitted in a compressed state is inserted into the stenosal portion of tubular organs of a living body such as an esophagus and the like. At this time, an endoscope is separately inserted to allow an operator to bring the tip end portion of the external tube 3 into a target position, i.e., in the stenosal portion of tubular organs, while observing the stent.

Once the tip end portion of the external tube 3 is inserted into the target position, the internal tube 5 is slidingly moved forward to push the stent 1 out of the tip end portion of the external tube 3. As illustrated in FIG. 2A, the leading end 1a of the stent 1 is first pushed out of the external tube 3 and expanded back to its original shape. In other words, the conventional stent inserting device is designed to ensure that the stent 1 is first expanded at its leading end 1a and then gradually expanded toward its trailing end 1b. When completely pushed out of the external tube 3, the stent 1 is capable of expanding the stenosal portion as shown in FIG. 2B.

In case a vocal cord or other membranes is situated behind the trailing end 1b of the stent 1, the conventional stent inserting device suffers from a problem in that the trailing end 1b of the stent 1 is caught by the vocal cord or other membranes in the process of expanding the stent 1 sequentially from the leading end toward the trailing end, which may cause the stent 1 to be situated in a wrong posture.

In particular, it is difficult to accurately estimate the position in which the trailing end 1b of the stent 1 lies when the stent 1 is fully expanded over the entire length thereof. This is because there is a great difference between the stent length available when the stent 1 is held within the tip end of the external tube 3 in a compressed state and the stent length available when the stent 1 is expanded back to its original shape in the stenosal portion.

Such problems posed in situating the stent 1 make it difficult for an operator to perform the stent inserting operation and also inflict physical or metal pains on a patient. In the worst circumstances, the stent inserting operation needs to be performed once again from the beginning.

SUMMARY OF THE INVENTION

In view of the above-noted and other problems inherent in the prior art, it is an object of the present invention to provide a stent inserting device that can allow a stent to be first expanded at its trailing end and then gradually expanded toward its leading end within a stenosal portion of tubular organs and, therefore, can be effectively used in treating the stenosal portion where the position of a trailing end of the stent needs to be controlled accurately.

Another object of the present invention is to provide a stent inserting device capable of easily and accurately situating a trailing end of a stent in a target stenosal portion of tubular organs of a living body without inflicting a physical or mental pain on a patient.

In accordance with the present invention, there is provided a stent inserting device for use in inserting a self-expandable stent with leading and trailing ends into a tubular organ of a living body, comprising: a grip body; an elongated flexible external tube attached to a front end of the grip body; an elongated flexible push member movably inserted into the external tube from a rear end of the grip body; and a tubular cap for removably receiving the stent in a compressed state, the tubular cap having a front end operatively connected to the push member and a rear end slidably fitted to a front end of the external tube, wherein the stent inserting device is designed to hold the stent within the tubular cap in such a manner that the stent is first expanded at the trailing end and then gradually expanded toward the leading end when the tubular cap is pushed away from the front end of the external tube by means of the push member.

The stent inserting device may further comprise a movable internal tube positioned between the external tube and the push member for movement toward and away from the tubular cap.

The push member may be configured to extend into the tubular cap and is fixedly secured to the front end of the tubular cap.

BRIEF DESCRIPTION OF THE DRAWINGS

The above and other objects and features of the present invention will become apparent from the following description of preferred embodiments, given in conjunction with the accompanying drawings, in which.

DETAILED DESCRIPTION OF THE PREFERRED EMBODIMENTS

Preferred embodiments of a stent inserting device in accordance with the present invention will now be described in detail with reference to the accompanying drawings.

Figure 1:
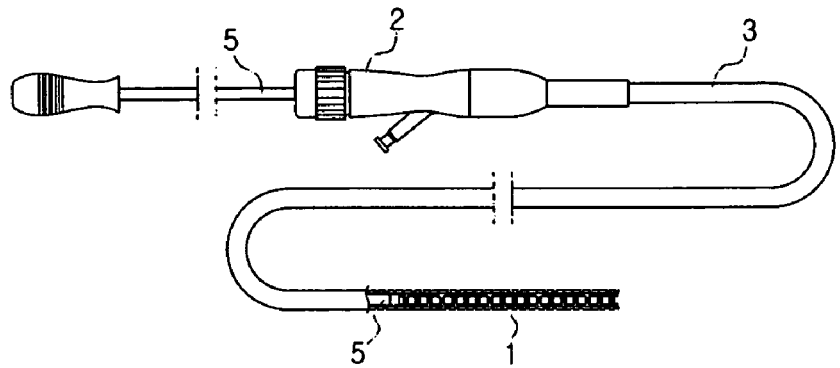
FIG. 1 is a view showing one example of conventional stent inserting devices.
Figure 2A:
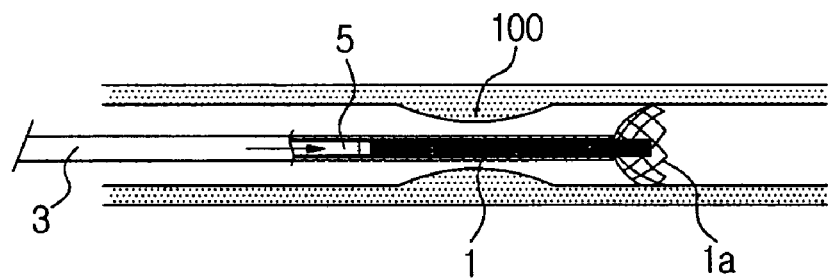
FIGS. 2A and 2B are section views illustrating a process of situating a stent in a stenosal portion by use of the conventional stent inserting device shown in FIG. 1.
Figure 2B:
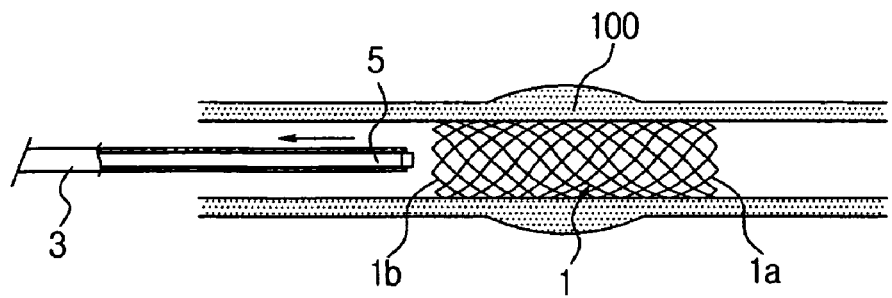
Figure 3:
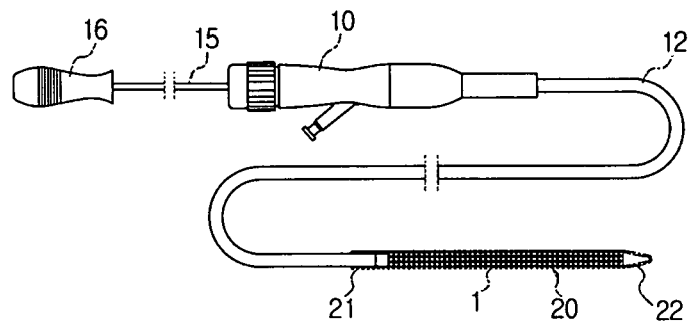
FIG. 3 is a view showing a stent inserting device in accordance with one embodiment of the present invention.
Figure 4:
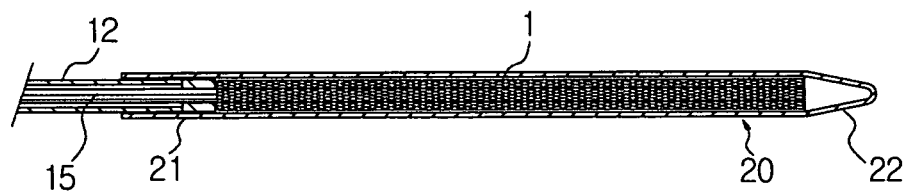
FIG. 4 is an enlarged section view illustrating major parts of the stent inserting device shown in FIG. 3.

Referring to FIGS. 3 and 4, there is shown a stent inserting device in accordance with one embodiment of the present invention, which is used in inserting a self-expandable stent 1 with leading and trailing ends into a tubular organ of a living body. The stent inserting device of the present embodiment includes a grip body 10, an elongated flexible external tube 12 attached to a front end of the grip body 10, an elongated flexible push member 15 movably inserted into the external tube 12 from a rear end of the grip body 10 and a tubular cap 20 for removably receiving the stent 1 in a compressed state, the tubular cap 20 having a front end 22 operatively connected to the push member 15 and a rear end 21 slidably fitted to a front end of the external tube 12.

The stent inserting device of the present embodiment is designed to hold the stent 1 within the tubular cap 20 in such a manner that the stent 1 is first expanded at the trailing end and then gradually expanded toward the leading end when the tubular cap 20 is pushed away from the front end of the external tube 12 by means of the push member 15.

The front end 22 of the tubular cap 20 is formed into a round shape so that it can assist in smoothly inserting the tubular cap 20 into the tubular organ of the living body. The push member 15 is configured to extend into the tubular cap 20 and is fixedly secured to the front end 22 of the tubular cap 20. A handle 16 is attached to a rear end of the push member 15.

Next, description will be made on an operation of the stent inserting device configured as above.

First, a stent 1 having a suitable size is selected depending on the diameter and length of a target lesion 100, e.g., a stenosal portion, present in a tubular organ of a living body. Then, the stent 1 is received within the tubular cap 20 in a compressed state. The rear end 21 of the tubular cap 20 is fitted to the front end of the external tube 12.

Once the preparation work is finished in this manner, the external tube 12 is inserted into the tubular organ of the living body and situated in alignment with the target lesion 100 of the tubular organ, e.g., a blood vessel. The stent insertion operation is visually monitored by use of an endoscope which is inserted into the tubular organ in parallel with the external tube 12. At this time, the rear end 21 of the tubular cap 20, more precisely, the trailing end 1b of the stent 1 is situated in alignment with the rear end of the target lesion 100.

Figure 5A:
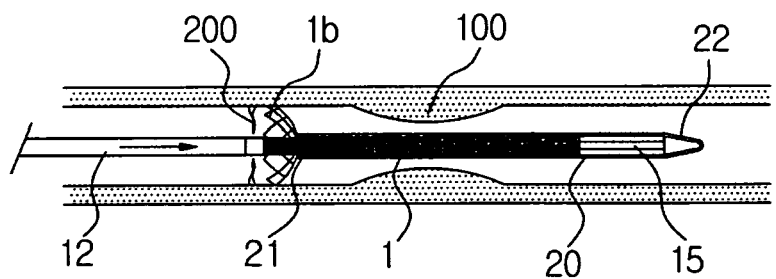
FIGS. 5A and 5B are section views illustrating a process of situating a stent in a stenosal portion by use of the stent inserting device shown in FIG. 3.
Figure 5B:
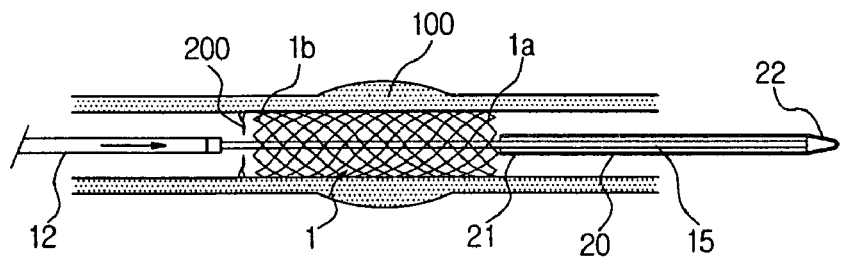

In this state, if the push member 15 is pushed forward while holding the grip body 10, the tubular cap 20 connected to the front end of the push member 15 is caused to move forward away from the external tube 12. Thus, the stent 1 is expanded at the trailing end 1b thereof as illustrated in FIG. 5A. As the tubular cap 20 continues to move forward, the stent 1 is gradually expanded toward the leading end 1a thereof and, at last, fully expanded over the entire length as illustrated in FIG. 5B. When fully expanded, the stent 1 is returned back to its original shape, thereby expanding the target lesion 100, i.e., the stenosal portion of the tubular organ.

After the stent 1 has been situated in the target lesion 100, the push member 15 is pulled backward so that the tubular cap 20 can be moved backward through the stent 1. Then, the external tube 12 is removed from the tubular organ of the living body together with the tubular cap 20.

With the stent inserting device of the present embodiment as described above, the stent 1 is first expanded at the trailing end 1b and then gradually expanded toward the leading end 1a within the target lesion 100, i.e., the stenosal portion of the tubular organ. Therefore, the stent inserting device can be effectively used in treating the stenosal portion of an esophagus or the like where the position of the trailing end 1b of the stent 1 must be controlled accurately to avoid interference with a vocal cord 200 or other membranes situated behind the trailing end 1b of the stent 1.

Figure 6:
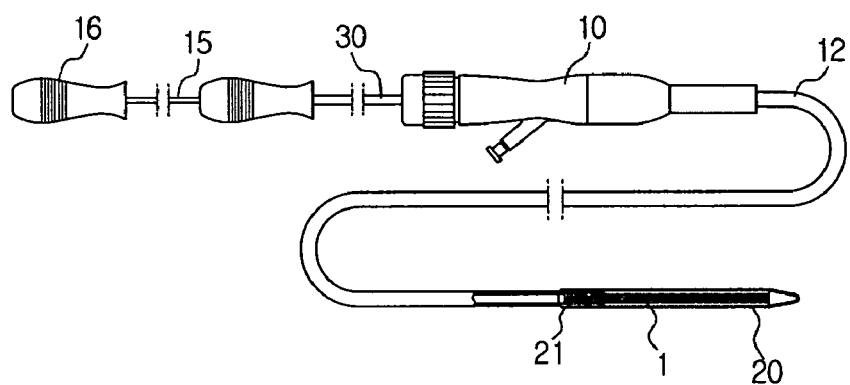
FIG. 6 is a view showing a stent inserting device in accordance with another embodiment of the present invention.
Figure 7:
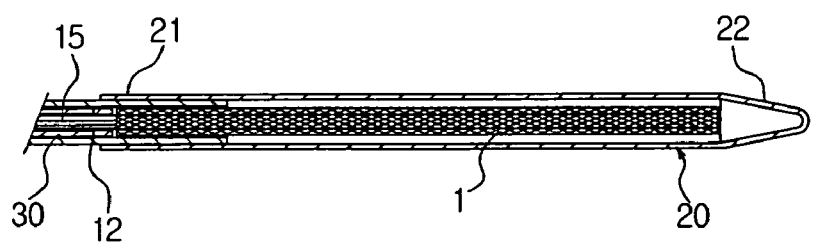
FIG. 7 is an enlarged section view illustrating major parts of the stent inserting device shown in FIG. 6.

Turning to FIGS. 6 and 7, there is shown a stent inserting device in accordance with another embodiment of the present invention, which is used in inserting a self-expandable stent 1 with leading and trailing ends into a tubular organ of a living body. As in the preceding embodiment, the stent inserting device of the present embodiment includes a grip body 10, an elongated flexible external tube 12 attached to a front end of the grip body 10, an elongated flexible push member 15 movably inserted into the external tube 12 from a rear end of the grip body 10 and a tubular cap 20 for removably receiving the stent 1 in a compressed state, the tubular cap 20 having a front end 22 operatively connected to the push member 15 and a rear end 21 slidably fitted to a front end of the external tube 12.

Unlike the preceding embodiment, the stent inserting device of the present embodiment further includes a movable internal tube 30 positioned between the external tube 12 and the push member 15 for movement toward and away from the tubular cap 20. An annular space for receiving the trailing end of the stent 1 is left between the front end of the internal tube 30 and the front end of the external tube 12.

The stent inserting device of the present embodiment is designed to hold the stent 1 within the tubular cap 20 and also within the front end of the external tube 12 in such a manner that the stent 1 is first expanded at a portion near the trailing end and then gradually expanded toward the trailing end and then the leading end when the tubular cap 20 is pushed away from the front end of the external tube 12 by means of the push member 15.

The front end 22 of the tubular cap 20 is formed into a round shape so that it can assist in smoothly inserting the tubular cap 20 into the tubular organ of the living body. The push member 15 is configured to extend into the tubular cap 20 and is fixedly secured to the front end 22 of the tubular cap 20. A handle 16 is attached to a rear end of the push member 15.

Next, description will be made on an operation of the stent inserting device configured as above.

First, the stent 1 is received within the tubular cap 20 in a compressed state so that the trailing end of the stent 1 can lie inside the front end of the external tube 12. The rear end 21 of the tubular cap 20 is fitted to the front end of the external tube 12.

Once the preparation work is finished in this manner, the external tube 12 is inserted into the tubular organ of the living body and situated in alignment with the target lesion 100 of the tubular organ, e.g., a blood vessel. The stent insertion operation is visually monitored by use of an endoscope which is inserted into the tubular organ in parallel with the external tube 12. At this time, the rear end 21 of the tubular cap 20, more precisely, the trailing end 1*b* of the stent 1 is situated in alignment with the rear end of the target lesion 100.

Figure 8A:
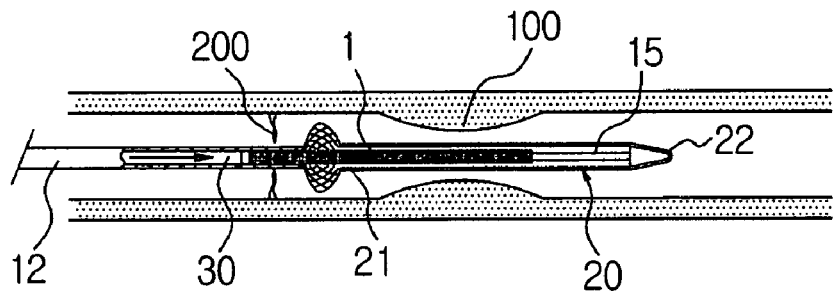
FIGS. 8A, 8B and 8C are section views illustrating a process of situating a stent in a stenosal portion by use of the stent inserting device shown in FIG. 6.
Figure 8B:
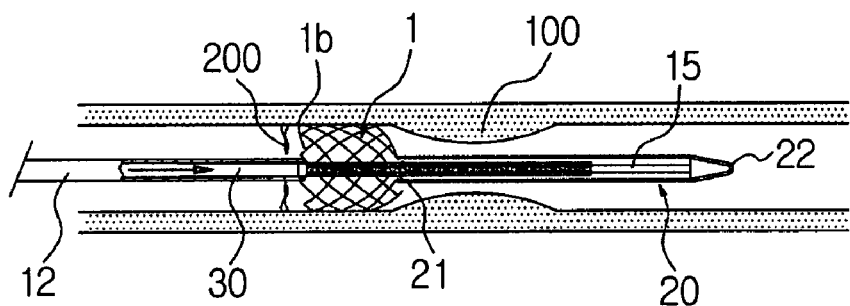

In this state, if the push member 15 is pushed forward while holding the grip body 10, the tubular cap 20 connected to the front end of the push member 15 is caused to move forward away from the external tube 12. Thus, the stent 1 is expanded at a portion near the trailing end 1*b* thereof as illustrated in FIG. 8A. At this moment, the internal tube 30 is pushed forward so that the trailing end 1*b* of the stent 1 can be pushed out of the external tube 12 and expanded as illustrated in FIG. 8B.

Figure 8C:
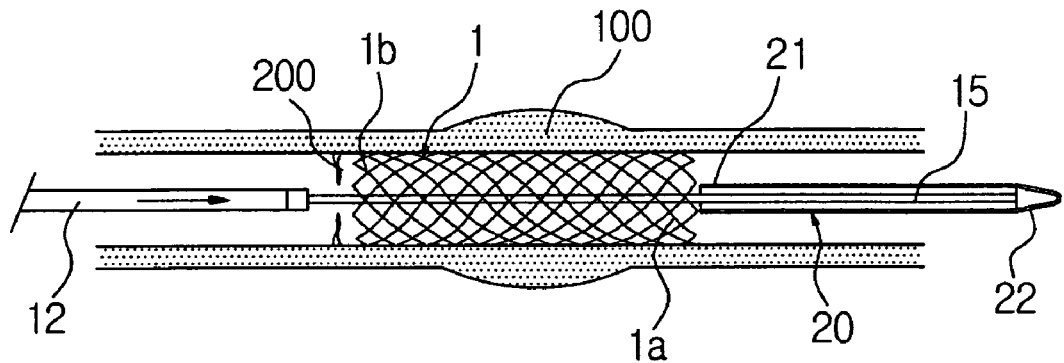

As the tubular cap 20 continues to move forward, the stent 1 is gradually expanded toward the leading end 1*a* thereof and, at last, fully expanded over the entire length as illustrated in FIG. 8C. When fully expanded, the stent 1 is returned back to its original shape, thereby expanding the target lesion 100, i.e., the stenosal portion of the tubular organ.

After the stent 1 has been situated in the target lesion 100, the push member 15 is pulled backward so that the tubular cap 20 can be moved backward through the stent 1. Then, the external tube 12 is removed from the tubular organ of the living body together with the tubular cap 20.

With the stent inserting device of the present embodiment as described above, the stent 1 is first expanded at the trailing end 1*b* and then gradually expanded toward the leading end 1*a* within the target lesion 100, i.e., the stenosal portion of the tubular organ. Therefore, the stent inserting device can be effectively used in treating the stenosal portion of an esophagus or the like where the position of the trailing end 1*b* of the stent 1 must be controlled accurately to avoid interference with a vocal cord 200 or other membranes situated behind the trailing end 1*b* of the stent 1.

As described hereinabove, the stent inserting device of the present invention can allow the stent to be first expanded at its trailing end and then gradually expanded toward its leading end within a stenosal portion of tubular organs and, therefore, can be effectively used in treating the stenosal portion where the position of a trailing end of the stent needs to be controlled accurately. Furthermore, the stent inserting device of the present invention is capable of easily and accurately situating the trailing end of the stent in the stenosal portion of tubular organs without inflicting a physical or mental pain on a patient.

While certain embodiments of the present invention have been described hereinabove, the present invention is not limited to these embodiments. It will be understood by those skilled in the art that various changes and modifications may be made without departing from the scope of the invention defined in the claims.

What is claimed is:

1. A stent inserting device for use in inserting a self-expandable stent with leading and trailing ends into a tubular organ of a living body, comprising:
   a grip body;
   an elongated flexible external tube attached to a front end of the grip body;
   an elongated flexible push member movably inserted into the external tube from a rear end of the grip body;
   a tubular cap for removably receiving the stent in a compressed state, the tubular cap having a front end operatively connected to the push member and a rear end slidably fitted over and surrounding a front end of the external tube; and
   a movable internal tube positioned between the external tube and the push member for movement toward and away from the tubular cap,
   wherein the stent is held entirely within the tubular cap to first expand the stent at a position near the trailing end thereof in response to the tubular cap being pushed away from the front end of the external tube by the push member and to further expand the stent at the trailing end thereof in response to the movable internal tube being pushed toward the tubular cap.

2. The stent inserting device as recited in claim 1, wherein the push member is configured to extend into the tubular cap and is fixedly secured to the front end of the tubular cap.

3. The stent inserting device as recited in claim 1, wherein the front end of the external tube extends further toward the leading end of the stent than a front end of the movable internal tube.

4. A stent inserting device for use in inserting a self-expandable stent with leading and trailing ends into a tubular organ of a living body, comprising:
   a grip body;
   an elongated flexible external tube attached to a front end of the grip body;
   an elongated flexible push member movably inserted into the external tube from a rear end of the grip body; and
   a tubular cap for removably receiving the stent in a compressed state, the tubular cap having a front end operatively connected to the push member and a rear end slidably fitted over and surrounding a front end of the external tube,
   wherein the stent is held entirely within the tubular cap to first expand the stent at a position near the trailing end thereof in response to the tubular cap being pushed away from the front end of the external tube by the push member.

* * * * *